(12) United States Patent
Velthaus et al.

(10) Patent No.: US 10,088,512 B2
(45) Date of Patent: Oct. 2, 2018

(54) VECTOR NETWORK ANALYZER

(71) Applicant: FRAUNHOFER-GESELLSCHAFT ZUR FÖRDERUNG DER ANGEWANDTEN FORSCHUNG E.V., München (DE)

(72) Inventors: Karl-Otto Velthaus, Kleinmachnow (DE); Thorsten Göbel, Berlin (DE); Jung Han Choi, Berlin (DE)

(73) Assignee: FRAUNHOFER-GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 0 days.

(21) Appl. No.: 15/748,193

(22) PCT Filed: Jun. 7, 2016

(86) PCT No.: PCT/EP2016/062897
§ 371 (c)(1),
(2) Date: Jan. 28, 2018

(87) PCT Pub. No.: WO2017/017579
PCT Pub. Date: Feb. 2, 2017

(65) Prior Publication Data
US 2018/0224489 A1 Aug. 9, 2018

(30) Foreign Application Priority Data

Jul. 28, 2015 (DE) .................. 10 2015 214 289

(51) Int. Cl.
*G01R 27/28* (2006.01)
*G01N 21/3581* (2014.01)
(Continued)

(52) U.S. Cl.
CPC .......... *G01R 27/28* (2013.01); *G01N 21/3581* (2013.01); *G01R 23/14* (2013.01); *G02F 2/002* (2013.01); *G02F 2203/13* (2013.01)

(58) Field of Classification Search
CPC .... G01R 27/28; G01R 23/14; G01N 21/3581; G02F 2/002; G02F 2203/13
See application file for complete search history.

(56) References Cited

U.S. PATENT DOCUMENTS 6,348,683 B1 2/2002 Verghese et al.
7,291,839 B1 11/2007 Demers et al.
(Continued)

FOREIGN PATENT DOCUMENTS

DE 102 46 700 A1 4/2004
DE 10 2010 019134 A1 11/2011
EP 2 488 917 B1 9/2014

OTHER PUBLICATIONS

Criado, A.R. et al., "New concepts for a photonic vector network analyzer based on THz heterodyne phase-coherent techniques", Proceedings of the 7th European Microwave Integrated Circuits Conference, Amsterdam, Oct. 29-30, 2012, pp. 540-543.
(Continued)

*Primary Examiner* — Jerry Rahll
(74) *Attorney, Agent, or Firm* — Maschoff Brennan

(57) ABSTRACT

It is provided a vectorial network analyzer, comprising an input and output measuring device; a beat source for generating an optical beat signal; an optical transmission device which divides the optical beat signal into at least one first and one second partial signal, wherein the transmission device conducts the first partial signal to at least one terahertz transmitter and the second partial signal to at least one terahertz receiver and/or to at least one terahertz reference receiver; and a phase changing unit for varying the
(Continued)

phase of the first and/or the second partial signal of the optical beat signal.

15 Claims, 7 Drawing Sheets

(51) Int. Cl.
  *G02F 2/00* (2006.01)
  *G01R 23/14* (2006.01)

(56) References Cited

U.S. PATENT DOCUMENTS

| | | |
|---|---|---|
| 8,953,937 B2 | 2/2015 | Sartorius et al. |
| 2004/0066182 A1 | 4/2004 | Evers et al. |
| 2014/0270619 A1 | 9/2014 | Giboney |

OTHER PUBLICATIONS

Göbel, T. et al, "Continuous-wave terahertz system with electro-optical terahertz phase control", Electronics Letter, 44/14 (Jul. 3, 2008) 863-864.

Göbel, T. et al, "Single-sampling-point coherent detection in continuous-wave photomixing and millimeterwave measurement", Electronics Letter, 45/1 (Nov. 5, 2009) 65-66.

Nagatsuma, Tadao et al., "1.55-μm photonic systems for microwave and millimeterwave measurement", IEEE transactions on microwave theory and techniques, 49/10 (Oct. 10, 2001) 1831-1839.

Raemer, Jan Martin and Georg von Freymann, "A Terahertz Time-Domain Spectroscopy-Based Network Analyser", Journal of Lightwave Technology, 33/2 (Jan. 15, 2015) 403-407.

Stanze, D. et al, "High-speed coherent CW terahertz spectrometer", Electronics Letter, 47/23 (Nov. 10, 2011) 1292-1294.

Zhuang et al., "Photonic High-Bandwidth RF Splitter With Arbitrary Amplitude and Phase Offset", IEEE Photonics Technology Letters, vol. 26, No. 21, Nov. 1, 2014, pp. 2122-2125.

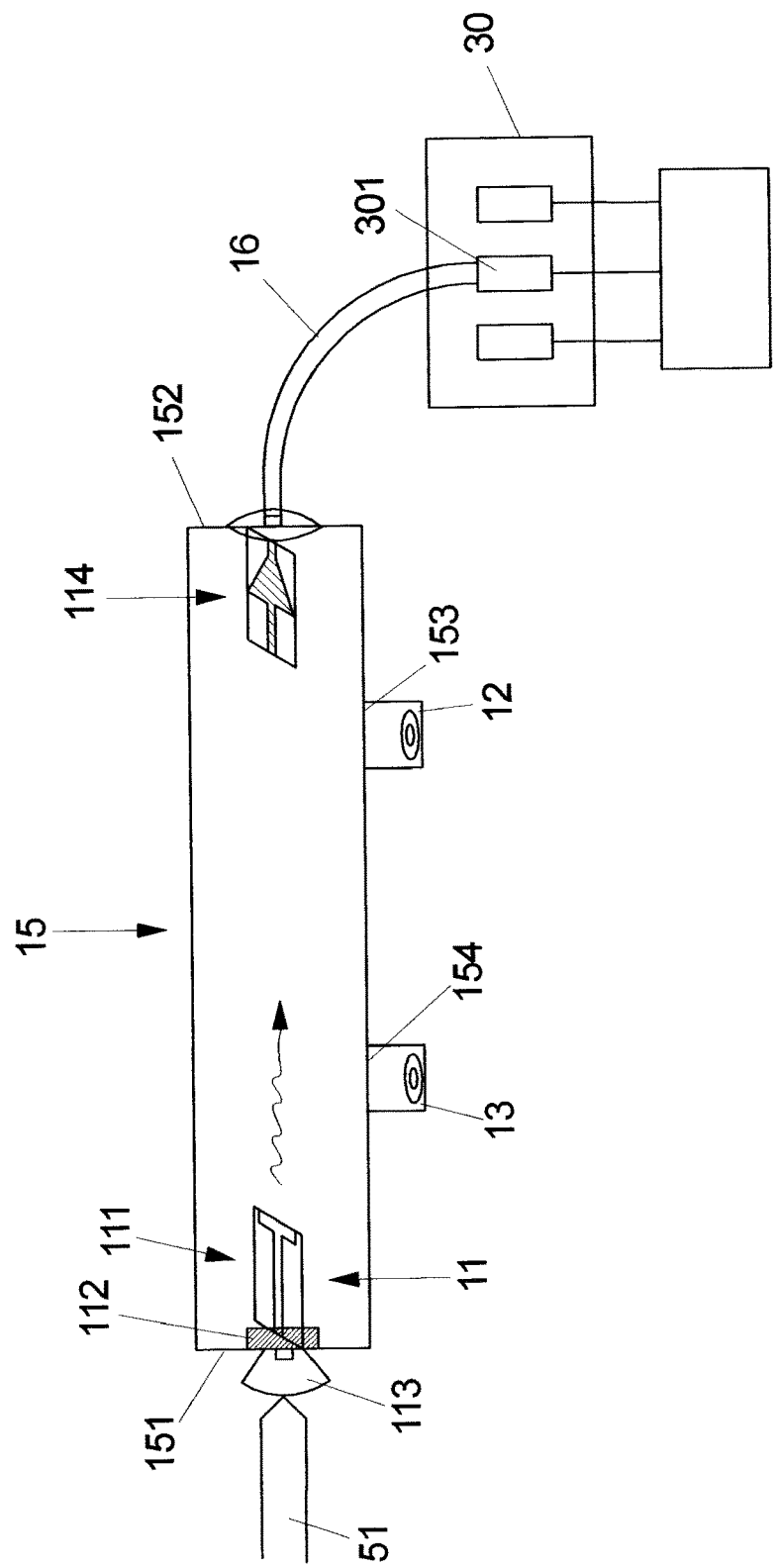

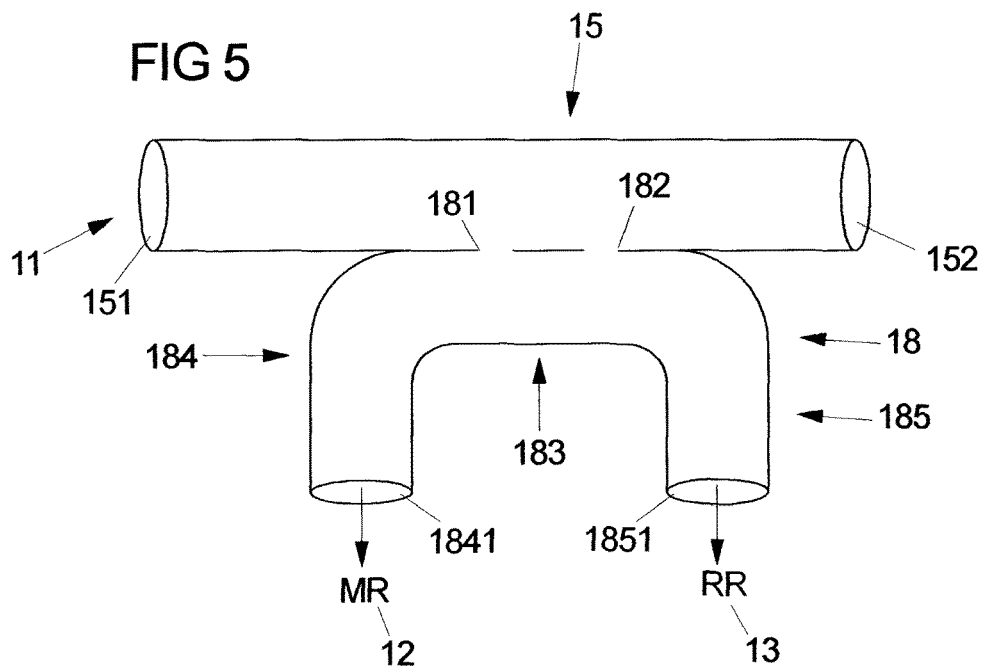
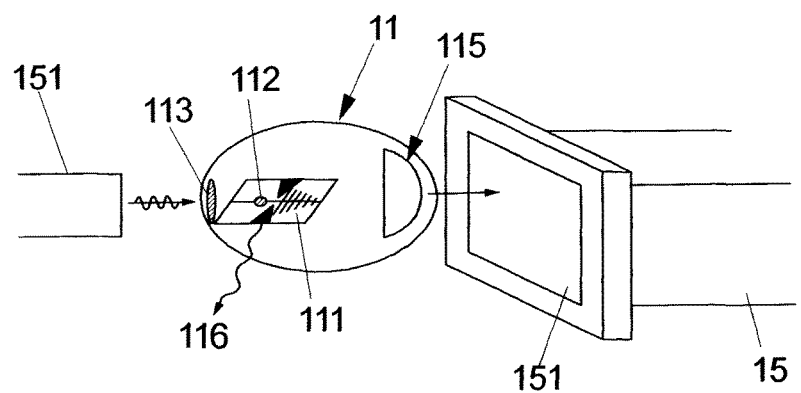
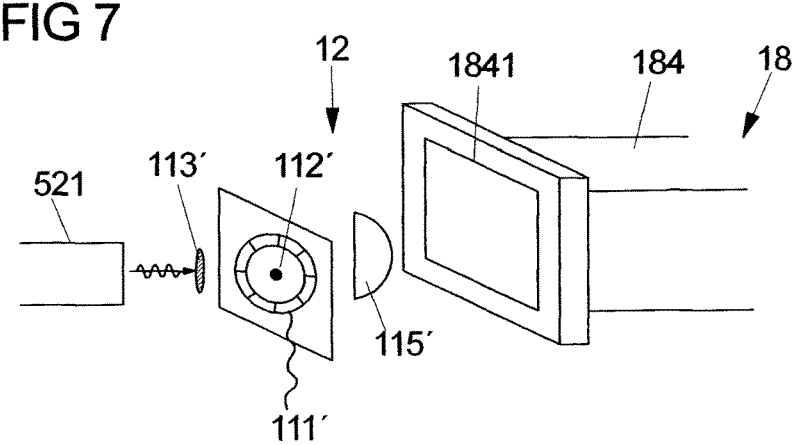

VECTOR NETWORK ANALYZER

CROSS-REFERENCE TO A RELATED APPLICATION

This application is a National Phase Patent Application of International Patent Application Number PCT/EP2016/062897, filed on Jun. 7, 2016, which claims priority of German Patent Application Number 10 2015 214 289.2, filed on Jul. 28, 2015.

BACKGROUND

This invention relates to a vectorial network analyzer.

From the prior art vectorial network analyzers are known, by means of which the reflection and/or transmission behavior (the "S-parameters") of an electronic component or a network can be measured in a frequency-dependent manner.

One difficulty consists in the generation and supply of a high-frequency electrical signal to the component to be measured, as the electrical losses for instance of flexible lines increase overproportionally towards high frequencies. At frequencies up to 100 GHz loss-reduced lines are used, which however only should have a length of some decimeters, so as not to significantly deteriorate the measurement signal. For generating frequencies above 100 GHz electronic mixer stages are used, which however are available only at very high costs. In addition, such mixer stages are bulky and lead to unflexible measurement set-ups, as they must be connected with the measurement object via a rigid hollow conductor. Furthermore, each mixer stage can only be used for a specific frequency range, wherein for each of the eight hollow conductor standards (WR8-WR1, from 90 GHz to 1.1 THz) one individual, complex electronic component each must be manufactured. Another possibility for carrying out high-frequency measurements is described in U.S. Pat. No. 6,348,683 B1. This measurement method, however, for example allows no determination of the phase position of all transmissive and reflected measurement signals that would be necessary for the realization of a two-port vector analyzer.

SUMMARY

The problem underlying the invention consists in providing a network analyzer as inexpensive and flexibly handleable as possible, which provides for a most comprehensive characterization of an electronic component in particular for frequencies up into the terahertz range.

This problem is solved by providing the vectorial network analyzer with features as described herein.

Accordingly, there is provided a vectorial network analyzer, comprising
an input measuring device, including:
a terahertz transmitter for applying a terahertz signal to an input of a measurement object;
a terahertz receiver for receiving a terahertz signal emitted via the input of the measurement object;
a terahertz reference receiver for receiving a part of the terahertz signal generated by the terahertz transmitter;
an output measuring device, including:
a terahertz transmitter for applying a terahertz signal to an output of the measurement object;
a terahertz receiver for receiving a terahertz signal emitted via the output of the measurement object;
a terahertz reference receiver for receiving a part of the terahertz signal generated by the terahertz transmitter;
a beat source for generating an optical beat signal;
an optical transmission device which divides the optical beat signal into at least one first and one second partial signal, wherein the transmission device conducts the first partial signal to at least one of the terahertz transmitters and the second partial signal to at least one of the terahertz receivers and/or at least one of the terahertz reference receivers; and
a phase changing unit (a phase influencing element) for varying the phase of the first and/or the second partial signal of the optical beat signal.

The network analyzer according to the invention thus is a complete two-port network analyzer, wherein the transmission and the reflection of a terahertz measurement signal fed into the measurement object can each be measured at an input and at an output of the measurement object. It also is possible to each determine a reference signal of the terahertz signal generated by the terahertz transmitter, which in particular serves for the characterization of this terahertz signal. With the phase changing unit it also is possible in particular to adjust a phase shift between the first and the second (optical) partial signal, which in particular provides for a determination of the phase position of the measurement signals generated by the terahertz receivers. The terahertz receivers in particular are coherent receivers, as for example in U.S. Pat. No. 6,348,683 B1. In so far, reference is made expressly to this document.

According to one aspect of the invention the input measuring device and/or the output measuring device includes a waveguide acting as directional coupler, via which the terahertz signal of the terahertz transmitter can be conducted to the measurement object and the terahertz reference receiver, and the terahertz signal emitted by the measurement object can be conducted to the terahertz receiver. The waveguide in particular is a hollow waveguide. This variant of the invention, however, is not limited to waveguides in the form of hollow waveguides, but in principle any waveguiding structures can be used; for example also photonic crystals. The waveguide for example at least sectionally extends linearly and in principle can have any cross-section, for example a circular or rectangular (in particular square) cross-section. In addition, the waveguide includes an input (in particular in the form of an opening formed in a first end face of the waveguide) and an output (in particular in the form of an opening formed in a second end face of the waveguide facing away from the first end face), wherein the terahertz transmitter in particular is arranged at and/or in the input. It is also conceivable that more than one input measuring device and/or more than one output measuring device are present.

The terahertz transmitter for example is a device which comprises a photomixer coupled/integrated with an antenna. The photomixer in turn consists either of an optical photoconductor or an optical photodiode. In particular, a terahertz transmitter or a terahertz receiver is understood to be a transmitter or receiver which generates electromagnetic radiation with frequencies up into the terahertz range, in particular the range between 90 GHz and 3 THz is covered.

The construction of the terahertz receiver can correspond to the construction of the terahertz transmitter, wherein however the photomixer and/or the antenna can have a different design (for example the terahertz receiver includes no photodiode, but a photoconductor). The terahertz transmitter and the terahertz receivers can be realized in a compact construction, so that the opto-electronic "sensing heads" of the network analyzer according to the invention, i.e. in particular the hollow waveguides with the respectively associated terahertz transmitters and terahertz receivers, likewise can have a construction which is compact in particular in comparison with the sensing heads of the known purely electrical network analyzers. For example, the approach according to the invention allows to replace expensive and awkwardly large electrical mixer stages by smaller sensing heads (with more compact opto-electrical transmitters and receivers). These opto-electrical transmitters and receivers are realized individually e.g. for each hollow conductor standard (W8-W1) according to which the hollow waveguides can be designed. The optical beat source (e.g. at least one laser of the optical beat source used as light source) as well as the phase changing unit can, however, remain unchanged for all frequencies (e.g. also up to above 1 THz). As a result, a small and hence flexible measurement system can be realized, which in particular can be manufactured at distinctly lower cost than conventional, purely electrical measurement systems (e.g. less expensive by the factor of 10).

The optical transmission device of the network analyzer according to the invention for example comprises at least one first optical waveguide (for example in the form of a glass fiber), via which the first optical partial signal can be conducted to at least one of the terahertz transmitters, and at least one second optical waveguide, via which the second optical partial signal can be conducted to at least one of the terahertz receivers and/or at least one of the terahertz reference receivers. The first and/or the second optical waveguide in particular are coupled with the respective photomixer of the terahertz transmitter, the terahertz receivers or the terahertz reference receivers, each for example via an imaging optical system (such as in the form of a lens).

It is also possible that the vectorial network analyzer according to the invention includes a further waveguide (e.g. in the form of a further hollow waveguide) coupled with the waveguide (formed e.g. as hollow waveguide), wherein at least one transition (in particular a through hole) is present, via which a terahertz signal can couple over from the waveguide into the further waveguide. For example, a first and a second transition is present, via which a terahertz signal can couple over from the waveguide into the further waveguide and get to the terahertz receiver and the terahertz reference receiver. In particular when using second hollow waveguides as first and second waveguide, the first and the second transition each are formed in particular by openings aligned with each other in side walls of the hollow waveguide and the further hollow waveguide. For example, the openings each are disposed in side portions of the hollow waveguide and the further hollow waveguide, which extend at least approximately parallel (and in particular linear) to each other.

To be able to couple a frequency range of the terahertz signals as broad as possible from the waveguide over into the further waveguide, it also is possible that more than two transitions are provided. Via the diameter and/or the distance of the transitions from each other, the coupling factor also can be defined with respect to coupling the terahertz waves from the waveguide over into the further waveguide.

According to another aspect of the invention the further waveguide has a first output via which a terahertz signal (e.g. the terahertz signal emitted by the measurement object, which is coupled over into the further hollow waveguide) can be conducted to the terahertz receiver. The output in particular is formed as an opening in an end face of the further waveguide facing the terahertz receiver. It is also possible that the further waveguide has a second output via which a terahertz signal (e.g. the terahertz signal of the terahertz transmitter coupled over into the further waveguide) can be conducted to the terahertz reference receiver. Analogous to the first output, the second output likewise is formed in particular as an opening (in a further end face) of the waveguide. It is conceivable that the further waveguide includes a linearly extending portion which extends parallel to at least one portion of the waveguide. In addition, the further waveguide can have end portions which extend at an angle to the linearly extending portion. For example, the further waveguide (in a lateral top view) is formed at least approximately U-shaped or V-shaped.

Moreover, it is possible that with the waveguide an (e.g. flexible) high-frequency line is coupled (such as a coaxial or coplanar line), via which the terahertz radiation exiting from the waveguide is conducted to the measurement object. For example, there is provided a converter via which the waveguide, i.e. the output of the waveguide on the side of the measurement object, is connected with the high-frequency line. It is also conceivable that a continuous waveguide (e.g. a continuous hollow waveguide) is used, which conducts the signal from the terahertz transmitter up to the measurement object.

According to another development, the network analyzer according to the invention includes an imaging element via which the terahertz signal of the terahertz transmitter can be coupled into the waveguide. The imaging element in particular is formed of a dielectric material or a metamaterial, wherein this for example is a lens which is formed for instance planar or at least partly spherical.

In addition, one imaging element each can be present, e.g. likewise a lens (for example formed as mentioned above), via which the terahertz waves are coupled out of the further waveguide. It is conceivable that to the outputs of the further waveguide one such imaging element each is associated, by means of which in particular the terahertz waves propagating in the further waveguide each are mapped onto the photomixer of the terahertz receiver or onto the photomixer of the terahertz reference receiver.

According to another exemplary embodiment of the network analyzer of the invention its phase changing unit includes a mechanically adjustable optical delay line. For example, the delay line comprises two redirecting elements arranged at an angle to each other, which jointly are linearly movable. Such mechanical delay lines, however, are known per se, so that they will not be discussed here in more detail.

It is also conceivable that the phase changing unit comprises a phase modulator. For example, this is a polarization-selective phase modulator which differently influences differently polarized components of the beat signal. For example, only one of the components of the optical beat signal is phase-shifted. In this way, a phase shift between the first and the second partial signal of the optical beat signal can be generated without a mechanical delay line. This method is described in particular in the patent EP 2 488 917 B1, to which reference in so far is made herewith expressly.

The optical beat source for example includes two lasers with slightly different emission wavelength. The emitted radiation of the two lasers is superimposed, whereby the optical beat signal is obtained. It is conceivable that for the superposition of the radiation generated by the lasers an optical coupler is used. For example, the radiation each emitted by the lasers is conducted into the coupler via a glass fiber. In addition, the coupler at the same time can serve to divide the beat signal generated by superimposing the laser radiation into the first and the second partial signal. For example, the coupler has two outputs via which the first and the second partial signal is conducted to at least one of the terahertz transmitters or to at least one of the terahertz receivers and/or to at least one of the terahertz reference receivers.

Moreover, it is conceivable that the phase changing unit (for example in the form of the phase modulator already mentioned above) is provided in a transmission line leading away from the coupler. The outgoing transmission line is realized e.g. by at least one glass fiber.

According to another aspect of the invention the beat source includes a two-mode laser which at the same time generates two modes of slightly different wavelength, wherein the modes are superimposed already in the laser and the laser thus directly emits the optical beat signal. The division of this beat signal into the first and the second partial signal can then be effected for example via a corresponding splitter.

BRIEF DESCRIPTION OF THE DRAWINGS

The invention will subsequently be explained in detail by means of exemplary embodiments with reference to the Figures.

FIG. 4 shows a schematic representation of a part of a network analyzer according to the invention.

FIG. 5 shows a schematic representation of a hollow conductor arrangement of the network analyzer according to the invention.

FIG. 6 shows a detail of the hollow conductor arrangement of FIG. 5.

FIG. 7 shows a further detail of the hollow conductor arrangement of FIG. 5.

DETAILED DESCRIPTION

Figure 1:
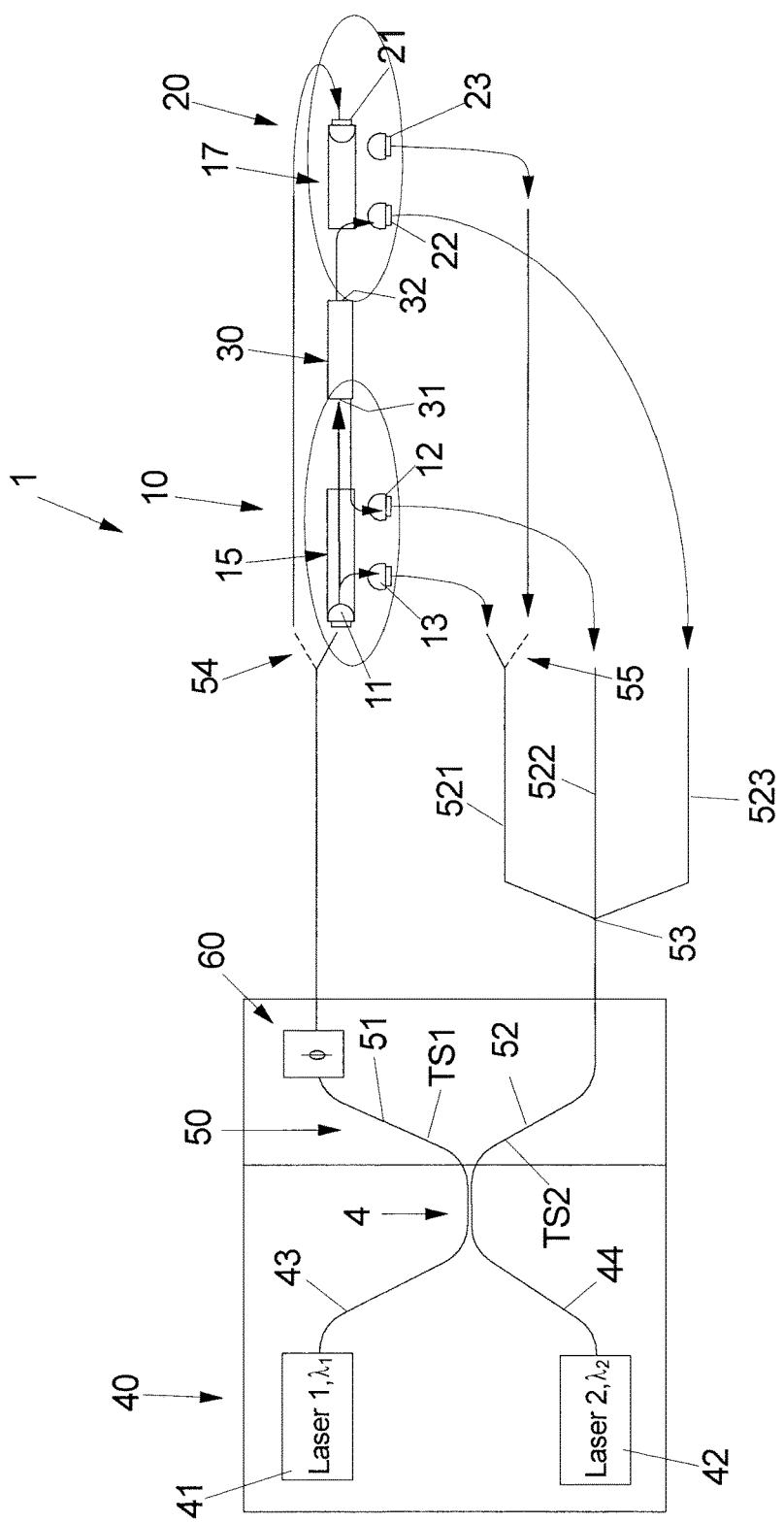
FIG. 1 shows a schematic representation of a network analyzer according to the invention.

The network analyzer 1 according to the invention as shown in FIG. 1 comprises an input measuring device 10 as well as an output measuring device 20. The input and output measuring devices 10, 20 each include a terahertz transmitter 11, 21, wherein the terahertz transmitter 11 of the input measuring device 10 serves to act on an input 31 of a measurement object 30 ("DUT") and the terahertz transmitter 21 of the output measuring device 20 serves to act on an output 32 of the measurement object 30.

The terahertz signal emitted by the terahertz transmitters 11, 21 each is transmitted to the measurement object 30 via a waveguide in the form of an (in particular rigid) hollow waveguide 15, 17, wherein the terahertz transmitters 11, 21 each are arranged at and/or in an output of the respective hollow waveguide 15, 17. An example for the arrangement of the terahertz transmitters 11, 21 on the hollow waveguides 15, 17 will be explained below with reference to FIG. 4. It has already been mentioned above that the invention is of course not limited to the use of a hollow waveguide for conducting the terahertz signals. Rather, any types of directionally coupling waveguides can be used in principle.

The input and output measuring devices 10, 20 furthermore each include a terahertz receiver 12, 22. The terahertz receiver 12 of the input measuring device 10 serves to receive a terahertz signal emitted via the input 31 of the measurement object 30, for example a signal reflected by the measurement object 30 or transmitted through the measurement object 30. Analogously, the terahertz receiver 12 of the output measuring device 20 is provided to receive a terahertz signal emitted via the output 32 of the measurement object 30.

The input and output measuring devices 10, 20 also each include a terahertz reference receiver 13, 23, with each of which a part of the terahertz radiation generated by the respective terahertz transmitter 11, 21 can be received. The reference receivers 13, 23 thus in particular serve to characterize the terahertz radiation emitted by the terahertz transmitters 11, 21. It should be noted that the positions of the terahertz receiver 12, 22 and of the terahertz reference receiver 13, 23 also can be interchanged, so that the terahertz receiver 12, 22 each can also be disposed closer to the terahertz transmitter 11, 21 than the terahertz reference receiver 13, 23. It is of course also conceivable that the terahertz receivers 12, 22 and the terahertz reference receivers 13, 23 at least approximately have the same distance from the respective terahertz transmitter 11, 21.

The vectorial network analyzer 1 in addition comprises an optical beat source 40 by means of which an optical beat signal can be generated. In the exemplary embodiment of FIG. 1 the beat source 40 comprises a first and a second laser 41, 42, which are slightly detuned relative to each other, i.e. have slightly different emission wavelengths $\lambda 1$, $\lambda 2$. The radiation generated by the lasers 41, 42 is superimposed in a coupler 4, whereby the desired optical beat signal is obtained. The light generated by the lasers 41, 42 is introduced into the coupler 4 via glass fibers 43, 44.

The coupler 4 also is part of an optical transmission device 50 of the network analyzer 1, which divides the optical beat signal into a first and a second partial signal TS1, TS2. The first optical partial signal TS1 can be conducted to the terahertz transmitter 11 of the input measuring device 10 and/or to the terahertz transmitter 21 of the output measuring device 20 via a glass fiber 51 connected with the coupler 4. The transmission device 50 furthermore comprises an optical switch 54 via which the light conducted by the glass fiber 51 (i.e. the first partial signal TS1) is supplied either to the terahertz transmitter 11 of the input measuring device 10 or to the terahertz transmitter 21 of the output measuring device 20.

Furthermore, the optical transmission device 50 comprises a further glass fiber 52 with which the second partial signal TS2 can be conducted to the coherent terahertz receivers 12, 23 and to the coherent reference receivers 13, 23 of the input and output measuring devices 10, 20. In particular, the second partial signal TS2 guided away from the coupler 4 via the glass fiber 52 is split up onto further glass fiber connections 521-523 via a splitter 53. The glass fiber connections 522 and 523 conduct the second partial signal TS2 to the terahertz receivers 12, 23, while via the glass fiber connection 521 the second partial signal TS2 is supplied either to the reference receiver 13 of the input measuring device 10 or to the reference receiver 23 of the output measuring device 20. It is possible that a further optical switch 55 is provided, via which either the reference receiver 13 or the reference receiver 23 is connected with that output of the coupler 4 (via the splitter 53) which emits the second partial signal TS2.

The network analyzer 1 according to the invention furthermore comprises a phase changing unit 60 by means of which the phase of the first partial signal TS1 can be changed relative to the phase of the second partial signal TS2. The phase changing unit 60 is coupled with the glass fiber 51, via which the first partial signal TS1 is transmitted. It is of course also conceivable that the phase changing unit 60 is arranged such that it does not act on the first partial signal TS1, but on the second partial signal TS2. This is realized in particular by the fact that the phase changing unit 60 is not coupled with the glass fiber 51, but with the glass fiber 52. Possible configurations of the phase changing unit 60 are shown in FIGS. 2 and 3.

Figure 2:
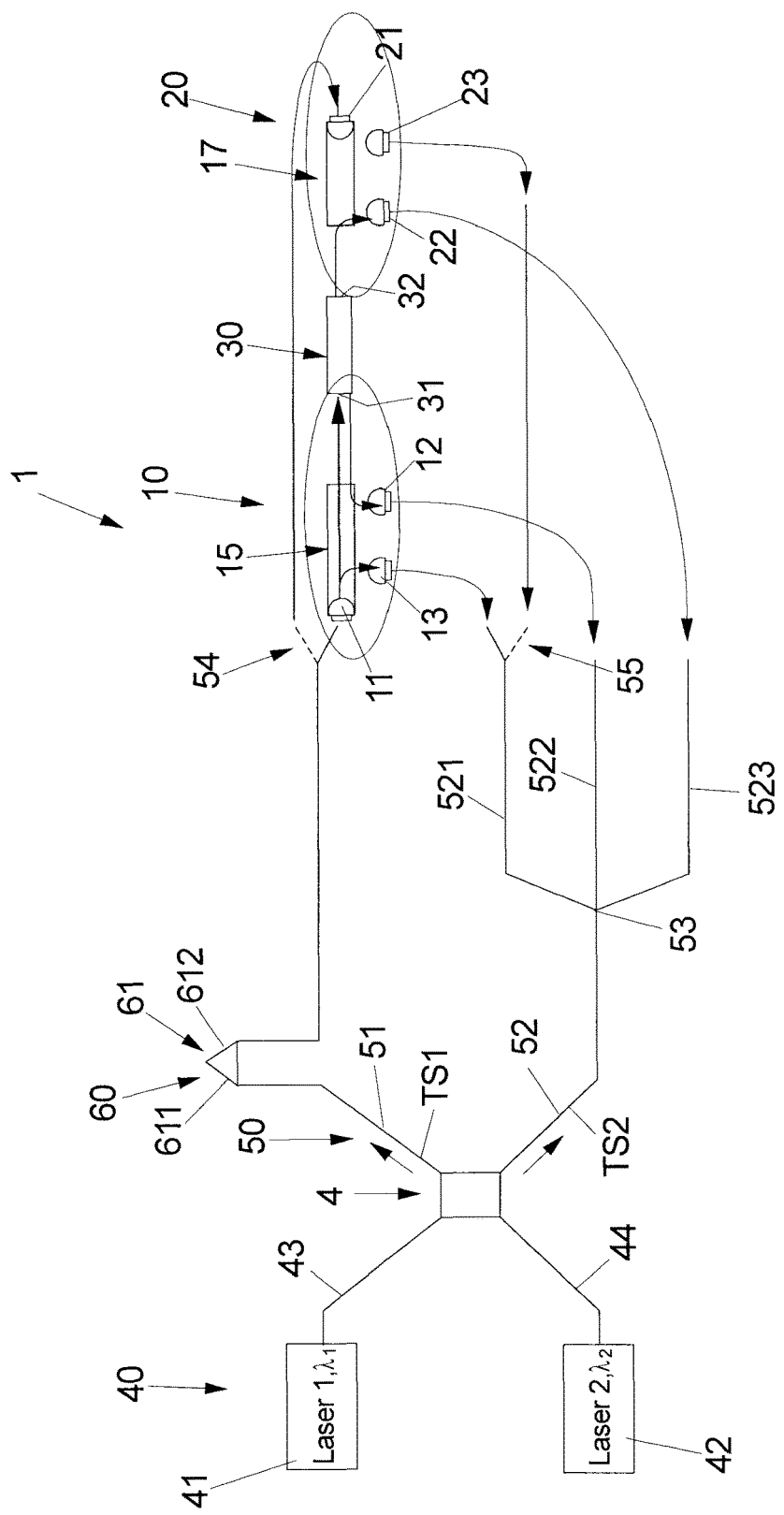
FIG. 2 shows a variant of the network analyzer of FIG. 1.

According to FIG. 2, which moreover corresponds to FIG. 1, the phase changing unit 60 comprises a mechanical optical delay line 61. More exactly, the mechanical delay line 61 includes two redirecting elements 611, 612 which are oriented at an angle to each other. The first partial signal TS1 conducted away from the coupler 4 via the glass fiber 51 is coupled into the delay line 61 by a free beam and is fed into a section of the glass fiber 51. Via the position of the redirecting elements 611, 612 the optical path length to be covered by the first partial signal TS1, and hence the phase of the first partial signal TS1 relative to the second partial signal TS2, is adjusted. Such delay devices, however, are known per se.

Figure 3:
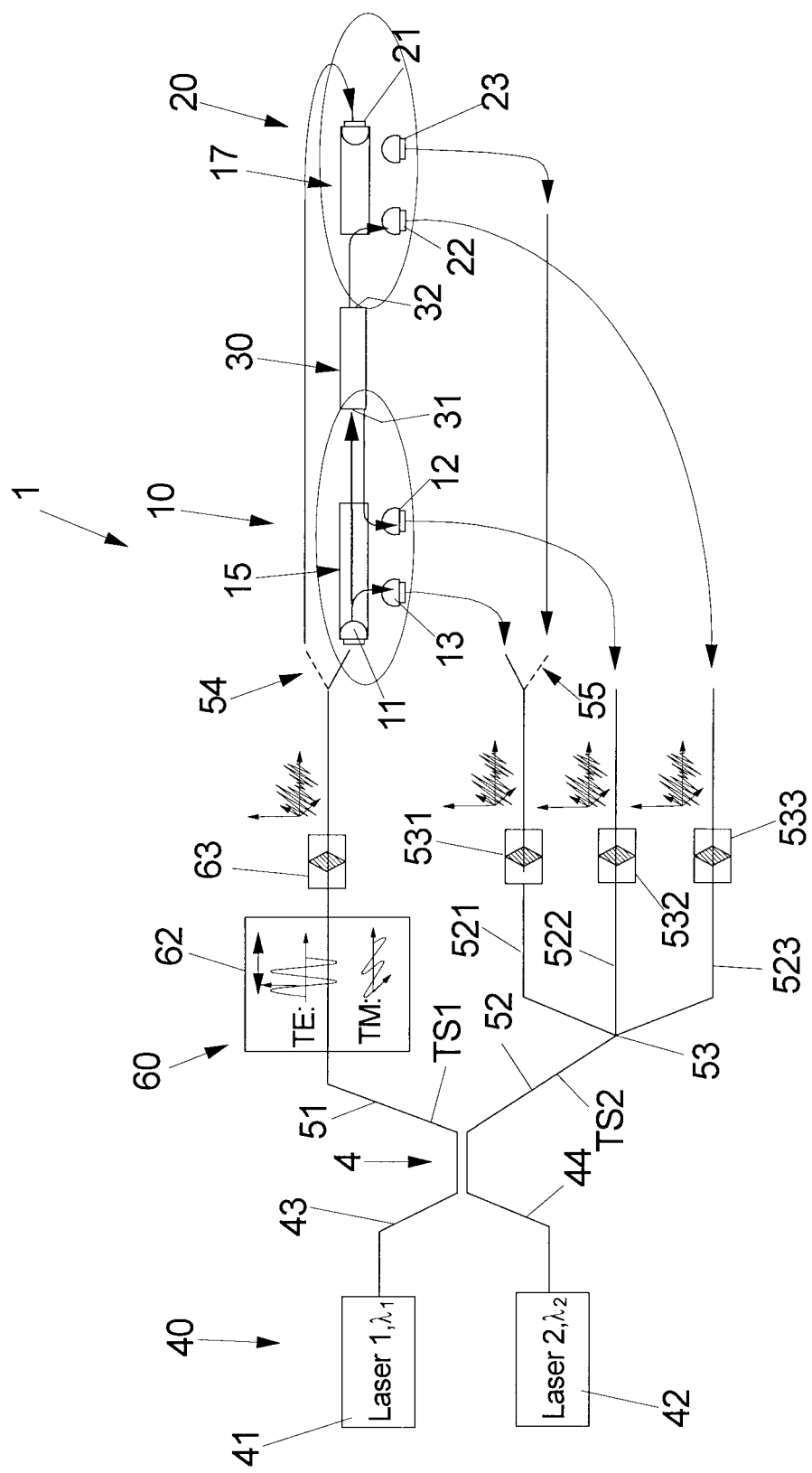
FIG. 3 shows a further variant of the network analyzer of FIG. 1.

FIG. 3 shows an alternative configuration of the phase changing unit 60. Accordingly, the phase changing unit 60 includes a polarization-selective phase modulator 62. The phase modulator 62 is designed such that it only acts on the phase of one of the two optical components of the optical beat signal. In other words, the phase modulator 62 only acts on the radiation generated by one of the two lasers (and forming one of the above-mentioned optical components of the beat signal). In the present case, the radiation of the first laser 41 has a TE polarization and the radiation of the second laser 42 has a TM polarization. The phase modulator 62 now is designed such that it only changes the phase of the TE-polarized light, i.e. the phase of the radiation of the first laser 41, while the phase of the TM-polarized radiation of the second laser 42 contained in the optical beat signal remains unchanged.

In a downstream polarizer 63 of the phase changing unit 60, which chiefly or exclusively transmits light of a polarization oriented at an angle with respect to the polarization of the light generated by the lasers 41, 42, the two components of the optical beat signal are superimposed, whereby the signal phase-shifted with respect to the second partial signal TS2 is obtained. This type of realization of the phase shift as such is described in the European Patent EP 2 488 917 B1 already mentioned above.

The second partial signal TS2 conducted to the terahertz receivers 12, 23 and to the terahertz reference receivers 13, 23 (i.e. the part each generated by the splitter 53) likewise is conducted through polarizers 531-533. The polarizers 531-533 in particular have similar or identical properties as the polarizer 63.

FIG. 4 shows an embodiment of the hollow waveguide 15 of the input measuring device 10 in an enlarged representation. The hollow waveguide 15 has an output in the form of an opening 151 formed in an end face of the hollow waveguide 15, to which the terahertz transmitter 11 is associated. As already mentioned above, the terahertz transmitter 11 includes a photodiode 112 coupled with an antenna 111. The terahertz transmitter 11 is at least partly located within the hollow waveguide 15, wherein the terahertz transmitter 11 for example protrudes beyond the opening 151 into the interior of the hollow waveguide 15. It is also conceivable that the terahertz transmitter 11 is located completely in the interior of the hollow waveguide 15 and merely the light coupled out of the glass fiber 51 is radiated onto the photodiode 112 of the terahertz transmitter 11 through the opening 151. It is of course also possible that the terahertz transmitter 11 completely is arranged outside the hollow waveguide 15.

For coupling the light exiting from the glass fiber 51 with the terahertz transmitter 11, i.e. with its photodiode 112, an imaging element in the form of a lens 113 can be provided. The terahertz waves emitted by the antenna 111 of the terahertz transmitter 11 propagate in the interior of the hollow waveguide 15 up to its rear exit (opening 152 which is located in the end face of the hollow waveguide 15 facing away from the terahertz transmitter 11). In the region of the opening 152 of the hollow waveguide 15 a converter 114 is disposed, via which the terahertz signal guided into the hollow conductor 15 can be coupled into a high-frequency line 16. This high-frequency line can be configured differently depending on the desired frequency band. Examples include hollow conductors, coaxial conductors or a coplanar line. The high-frequency line 16 conducts the terahertz signal to the measurement object 30, wherein the coaxial cable 16 in particular is connected with at least one contact surface of the measurement object 30, for example with a signal contact surface 301 of a GSG contact arrangement. The high-frequency line 16 together with the hollow waveguide 15 quasi forms a sensing head of the network analyzer.

The hollow waveguide 15 in addition includes openings 153, 154, via which a part of the terahertz signal guided in the hollow waveguide 15 is conducted to the terahertz receiver 12 or to the terahertz reference receiver 13. Coupling of the receivers 12, 13 in particular is effected analogous to the coupling of the terahertz transmitter 11 to the hollow waveguide 15. Coupling of the terahertz transmitter 21 or of the terahertz receivers 22, 23 to the hollow waveguide 17 of the output measuring device 20 in particular is effected in a way similar or identical to the coupling of the terahertz transmitter 21 or of the terahertz receivers 12, 13 of the input measuring device 10 to the hollow waveguide 15.

FIG. 5 illustrates another possibility for coupling a terahertz signal into the terahertz receiver (MR) 12 and into the terahertz reference receiver (RR) 13, wherein the positions of the terahertz receiver 12 and of the terahertz reference receiver 13 are interchanged with respect to the variant of FIG. 1.

Coupling into the terahertz receiver 12 and the terahertz reference receiver 22 of the out-coupling measuring device 20 can be realized identically.

According to FIG. 5, a further waveguide in the form of a further hollow waveguide 18 is present, which is coupled with the hollow waveguide 15. For coupling the two hollow waveguides 15, 18 a first and a second through hole 181, 182 is present, via which a part of a terahertz signal propagating in the hollow waveguide 15 can couple over into the further hollow waveguide 18. The through holes 181, 182 are formed by openings aligned with each other in side walls of the hollow waveguides 15, 18 adjacent to each other (in particular contacting each other). Via the distance of the through holes (in particular their centers) 181, 182, the coupling frequency range can be determined. For example, the distance is $\lambda/4$ ($\lambda$: wavelength of the terahertz waves propagating in the hollow waveguide 15). It is also conceivable that more than two through holes are provided, in particular in order to increase the frequency range of the waves coupling over. In addition, another directionally coupling structure (not formed as hollow waveguide) or a plurality of directionally coupling structures can be used instead of the hollow waveguides 15, 18, as already explained above.

The further hollow waveguide 18 has an at least approximately U-shaped form, wherein two end portions 184, 185 protrude (for example vertically) from a linearly extending center piece 183. In their end face, the end portions 184, 185 each have an output in the form of an opening 1841, 1851 via which the receivers, i.e. the terahertz receiver 12 and the terahertz reference receiver 13 are coupled with the further hollow waveguide 18. In particular, coupling of the receivers 12, 13 is effected in a way analogous to the coupling of the terahertz transmitter 11 with the hollow waveguide 15 as described in connection with FIG. 4.

One possibility for coupling the light exiting from the glass fiber 51 with the terahertz transmitter 11 is shown in FIG. 6 (region "P1" in FIG. 5). Accordingly, the light exiting from the glass fiber 51 is conducted to the terahertz transmitter 11 via the lens 113. The terahertz radiation emitted by the antenna 111 also is coupled into the hollow waveguide 15 via a suitable lens 115. It is also conceivable that the photodiode 112 and the antenna 111 of the terahertz transmitter 11, as shown in FIG. 4, at least partly are located in the interior of the hollow waveguide 15. Correspondingly, the lens 115 also would be arranged in the interior of the hollow waveguide 15. It is also conceivable that the terahertz transmitter 11 includes a reflector 116 arranged in front of the antenna 111 or formed by the antenna 111.

Coupling of the terahertz receivers 12, 13 can be effected analogously, as shown in FIG. 7. Accordingly, the second optical partial signal TS2 is conducted to the terahertz receiver 12 via the glass fiber 521 and via an imaging element in the form of a lens 113' focused onto a photodiode 112' of the terahertz receiver 12. The terahertz radiation exiting from the output 1841 of the end portion 184 of the further hollow waveguide 18 is coupled with an antenna 111' (in particular in the form of a broadband antenna) via a lens 115'. The current generated on reception of a terahertz wave by the terahertz receiver 12 can be evaluated with regard to the amplitude and phase of the received terahertz radiation in a manner known per se.

Figure 8:
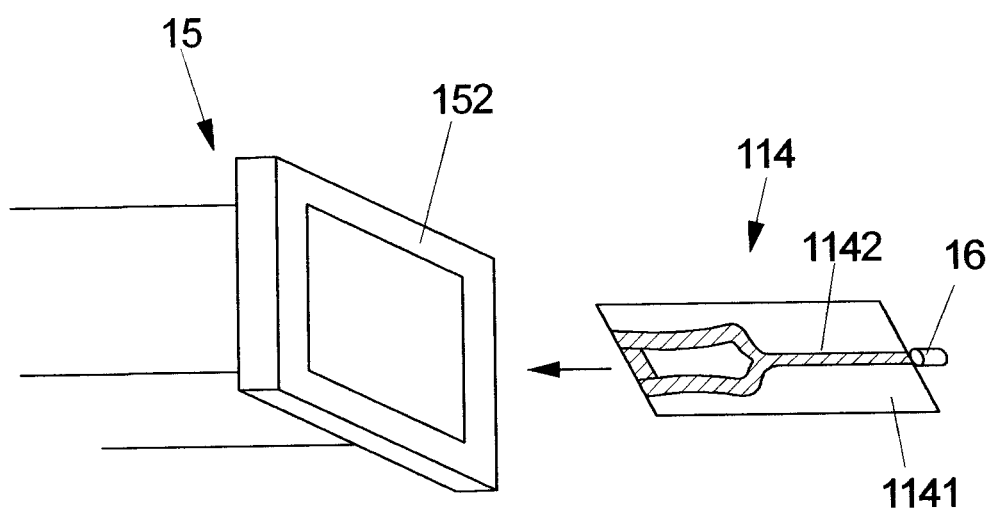
FIG. 8 shows a further detail of the hollow conductor arrangement of FIG. 5.

FIG. 8 shows the converter 114 arranged at or in the rear end of the hollow waveguide 15. The converter 114 includes a substrate 1141 on which a conductor structure 1142 is applied. The conductor structure 1142 tapers from the output opening 152 of the hollow waveguide 15 towards the coaxial cable 16. In particular, on its side facing the hollow waveguide 15 the conductor structure 1142 includes two (or more) conductor portions spaced from each other, which combine to form a single conductor portion on the side of the converter 114 facing the coaxial cable 16.

Figure 9:
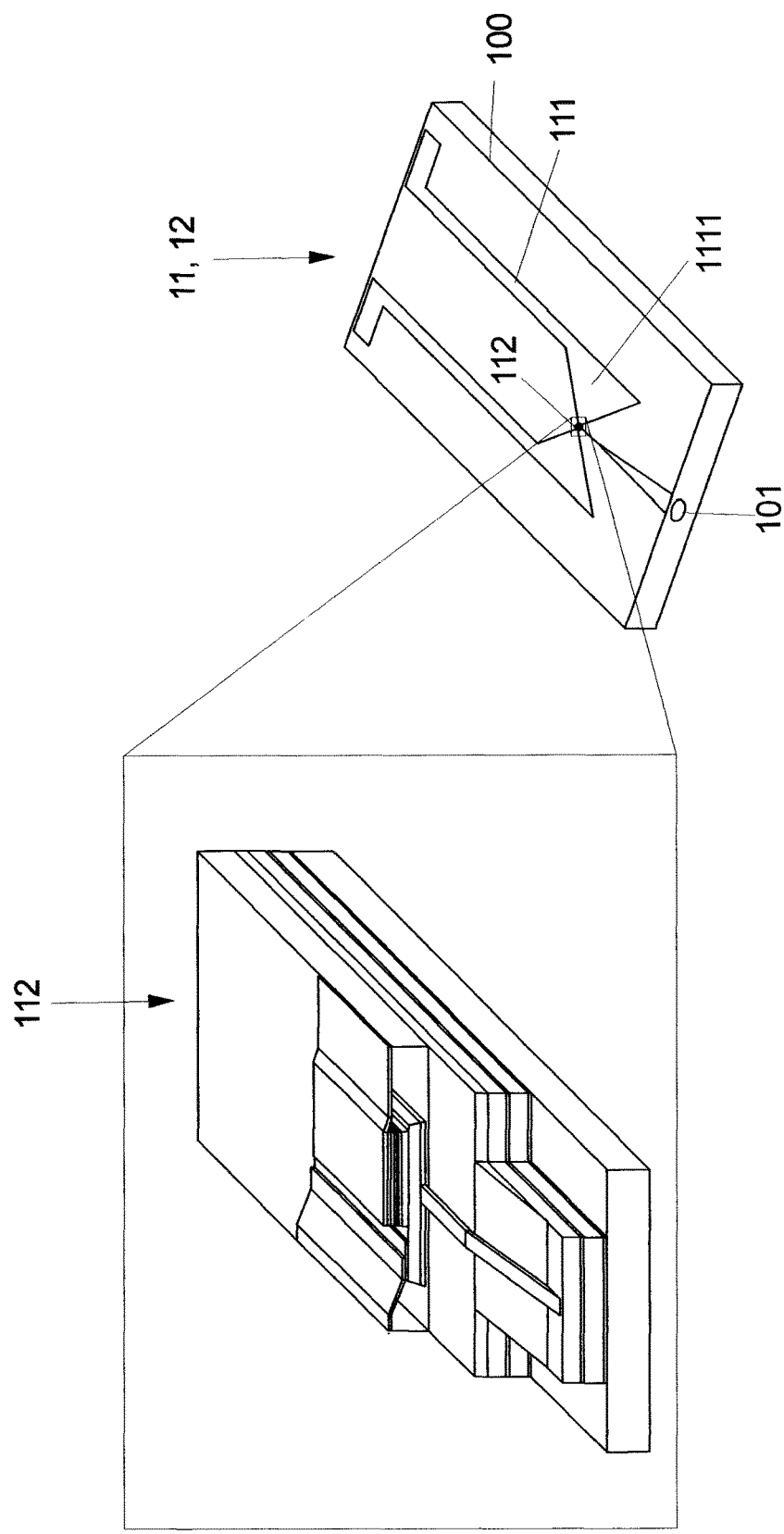
FIG. 9 shows a perspective view of a terahertz transmitter of a network analyzer according to the invention.

FIG. 9 shows a possible variant of the terahertz transmitters 11, 21. Accordingly, the terahertz transmitter 11, 21 comprises an antenna 1111 (such as in the form of a bow-tie antenna) and a photodiode 112 coupled with the antenna 1111 as well as a bias supply 111 connected with the antenna 1111. The bias supply 111, the bow-tie antenna 1111 and the photodiode 112 are located on a common substrate 100. It is conceivable that in or on the substrate 100 a waveguide 101 is formed, via which light is conducted to the photodiode 112. The photodiode 112 can be an integrated optical standard component, which e.g. is also used in data transmission systems.

The invention claimed is:

1. A vectorial network analyzer, comprising
an input measuring device, including:
 a terahertz transmitter for applying a terahertz signal to an input of a measurement object;
 a terahertz receiver for receiving a terahertz signal emitted via the input of the measurement object;
 a terahertz reference receiver for receiving a part of the terahertz signal generated by the terahertz transmitter;
an output measuring device, including:
 a terahertz transmitter for applying a terahertz signal to an output of the measurement object;
 a terahertz receiver for receiving a terahertz signal emitted via the output of the measurement object;
 a terahertz reference receiver for receiving a part of the terahertz signal generated by the terahertz transmitter;
a beat source for generating an optical beat signal;
an optical transmission device which divides the optical beat signal into at least one first and one second partial signal, wherein the transmission device conducts the first partial signal to at least one of the terahertz transmitters and the second partial signal to at least one of the terahertz receivers and/or at least one of the terahertz reference receivers; and
a phase changing unit for varying the phase of the first and/or the second partial signal of the optical beat signal.

2. The vectorial network analyzer according to claim 1, wherein the optical transmission device comprises at least one first optical waveguide via which the first partial signal can be conducted to at least one of the terahertz transmitters, and at least one second optical waveguide via which the second partial signal can be conducted to at least one of the terahertz receivers and/or at least one of the terahertz reference receivers.

3. The vectorial network analyzer according to claim 1, wherein the input measuring device and/or the output measuring device includes a waveguide, via which the terahertz signal of the terahertz transmitter can be conducted to the measurement object and the terahertz reference receiver, and the terahertz signal emitted by the measurement object can be conducted to the terahertz receiver.

4. The vectorial network analyzer according to claim 3, further comprising a further waveguide coupled with the waveguide, wherein at least one transition is present, via which a terahertz signal can couple over from the waveguide into the further waveguide.

5. The vectorial network analyzer according to claim 4, further comprising a first and a second transition, via which a terahertz signal can couple over from the waveguide into the further waveguide and can get to the terahertz receiver and the terahertz reference receiver.

6. The vectorial network analyzer according to claim 4, further comprising an imaging element via which a terahertz signal can be coupled out of the further waveguide.

7. The vectorial network analyzer according to claim 3, wherein the further waveguide includes a second output via which a terahertz signal can be conducted to the terahertz reference receiver.

8. The vectorial network analyzer according to claim 3, further comprising a high-frequency line coupled with the waveguide, via which terahertz radiation exiting from the waveguide can be conducted to the measurement object.

9. The vectorial network analyzer according to claim 8, further comprising a converter via which the waveguide is connected with the coaxial or coplanar line.

10. The vectorial network analyzer according to claim 3, further comprising an imaging element via which the terahertz signal of the terahertz transmitter can be coupled into the waveguide.

11. The vectorial network analyzer according to claim 3, wherein the further waveguide includes a first output via which a terahertz signal can be conducted to the terahertz receiver.

12. The vectorial network analyzer according to claim 1, wherein the phase changing unit comprises a mechanically adjustable optical delay line.

13. The vectorial network analyzer according to claim 1, wherein the phase changing unit comprises a phase modulator.

14. The vectorial network analyzer according to claim 1, wherein the beat source includes two lasers with different emission wavelength.

15. The vectorial network analyzer according to claim 1, wherein the beat source includes a two-mode laser.

\* \* \* \* \*